(12) United States Patent
Yuan et al.

(10) Patent No.: US 11,576,745 B2
(45) Date of Patent: Feb. 14, 2023

(54) HOLLOW VECTOR SUPPORT MULTIFUNCTIONAL PROTECTION DEVICE FOR MINIMALLY INVASIVE SURGERY

(71) Applicant: Peking University School and Hospital of Stomatology, Beijing (CN)

(72) Inventors: Fusong Yuan, Beijing (CN); Peijun Lyu, Beijing (CN)

(73) Assignee: Peking University School and Hospital of Stomatology, Beijing (CN)

( * ) Notice: Subject to any disclaimer, the term of this patent is extended or adjusted under 35 U.S.C. 154(b) by 402 days.

(21) Appl. No.: 16/968,972

(22) PCT Filed: May 13, 2019

(86) PCT No.: PCT/CN2019/086570
§ 371 (c)(1),
(2) Date: Aug. 11, 2020

(87) PCT Pub. No.: WO2020/199307
PCT Pub. Date: Oct. 8, 2020

(65) Prior Publication Data
US 2021/0169603 A1    Jun. 10, 2021

(30) Foreign Application Priority Data

Apr. 2, 2019    (CN) .......................... 201910261661.2

(51) Int. Cl.
*A61B 90/30*    (2016.01)
*A61B 90/00*    (2016.01)
(Continued)

(52) U.S. Cl.
CPC .......... *A61B 90/08* (2016.02); *A61B 17/0218* (2013.01); *A61B 90/30* (2016.02);
(Continued)

(58) Field of Classification Search
CPC ................... A61B 90/08; A61B 90/30; A61B 2090/08021; A61B 2017/00862;
(Continued)

(56) References Cited

U.S. PATENT DOCUMENTS 2,621,651 A    12/1952    Wallace
6,638,247 B1   10/2003    Selmon
(Continued)

FOREIGN PATENT DOCUMENTS

CN    1814317 A      8/2006
CN    102847228 A    1/2013
(Continued)

OTHER PUBLICATIONS

PCT Application No. PCT/CN2019/086570, International Search Report dated Oct. 8, 2020, 4 pages.

*Primary Examiner* — Kevin T Truong
*Assistant Examiner* — Diana Jones
(74) *Attorney, Agent, or Firm* — Avek IP, LLC

(57) ABSTRACT

Hollow vector support multifunctional protection devices and systems for minimally invasive surgery are disclosed. In an embodiment, a hollow vector support multifunctional protection device includes a protective head, a pitching mechanism for the protective head, an inner cylinder, an axial movement mechanism for the inner cylinder, and a shell. The protective head includes a flap ring, a plurality of first rotating shafts, a plurality of flaps uniformly arranged on the flap ring through the first rotating shafts, and a torsion spring arranged on the first rotating shafts. The torsion spring is configured to provide a force for opening the plurality of flaps along the first rotating shafts, and the first rotating shafts are provided with limiting structures configured to limit a maximum opening degree of the flaps.

9 Claims, 9 Drawing Sheets

(51) Int. Cl.
  *A61B 17/02* (2006.01)
  *A61B 17/00* (2006.01)
(52) U.S. Cl.
  CPC ............... *A61B 2017/00336* (2013.01); *A61B 2017/00539* (2013.01); *A61B 2017/00544* (2013.01); *A61B 2017/00862* (2013.01); *A61B 2090/08021* (2016.02); *A61B 2217/007* (2013.01)
(58) Field of Classification Search
  CPC .......... A61B 2217/007; A61B 17/0218; A61B 2017/00336; A61B 2017/00539; A61B 2017/00544
  See application file for complete search history.

(56) References Cited

U.S. PATENT DOCUMENTS

| | | | | |
|---|---|---|---|---|
| 2007/0149845 | A1* | 6/2007 | Kuhns | A61B 1/00087 600/101 |
| 2015/0272716 | A1* | 10/2015 | Pinchuk | A61F 2/0108 606/200 |
| 2016/0095689 | A1* | 4/2016 | Becking | A61B 17/221 606/200 |

FOREIGN PATENT DOCUMENTS

| | | |
|---|---|---|
| CN | 107041779 A | 8/2017 |
| CN | 206473344 U | 9/2017 |

\* cited by examiner

HOLLOW VECTOR SUPPORT MULTIFUNCTIONAL PROTECTION DEVICE FOR MINIMALLY INVASIVE SURGERY

CROSS REFERENCE TO RELATED APPLICATIONS

This application is the United States national stage entry under 35 U.S.C. 371 of PCT/CN2019/086570 filed on May 13, 2019, which claims priority to Chinese application number 201910261661.2 filed on Apr. 2, 2019, the disclosure of which are incorporated by reference herein in their entireties.

FIELD OF THE DISCLOSURE

The disclosure relates generally to medical equipment. More specifically, the disclosure relates to hollow vector support multifunctional protection devices for minimally invasive surgery.

BACKGROUND

It has been reported in the literature that, in recent years, the incidence of cavity and intestinal tracts diseases has increased year by year, especially malignant lesions, which may invade and compress the cavity and intestinal tracts and even obstruct the narrow part of the cavity and intestinal tracts, and may cause difficulty in food digestion absorption and defecation, seriously affecting people's life and quality of life. Approximately 1,000,000 new cases of intestinal malignant lesions occur annually throughout the world, with 7% to 29% of patients presenting with initial symptoms of acute complete or incomplete ileus. Because for intestinal obstruction, especially colorectal obstruction, preoperative intestinal preparation is not available, clinical treatment is difficult, and postoperative anastomotic leakage and serious infection are likely to occur, which is the most fundamental problem in surgical management of intestinal obstruction.

With the continuous progress of medical technology, endoscopic surgery and related surgical devices have become more and more popular. Exemplary devices include laparoscope, thoracoscope, esophagoscope, bronchoscope, gastroscope, enteroscope, cystoscope, hysteroscope, et cetera, which have laid the foundation for the implementation of minimally invasive surgery. However, for diseases of intestinal obstruction or extremely narrow lesion sites, the implementation of endoscopic surgery is difficult. For this reason, many domestic and international scholars have developed various methods of intraoperative proximal cavity and intestinal tract decompression and lavage, such as intraoperative cavity and intestinal tract lavage, temporary proximal colostomy, intraoperative transanal intubation decompression, postoperative decompression by preserving anal canal, et cetera. The development of the above methods provides conditions for the implementation of endoscopic surgery and is clinically popularized, but the above methods still have the defects of long operation time, pollution of abdominal cavities, disturbance of the internal environment of organisms due to losing of intestinal electrolytes and the like. It is reported, both domestically and internationally, that a variety of metallic stents have also been used as supports in the treatment of intestinal obstruction, i.e. placing a mesh stent at the site of intestinal stenosis to open the intestinal tract, so as to restore the site of stenosis or obstruction to patency, which creates conditions for surgery. The intestinal stent is suitable for patients with duodenal, small intestine, colon, rectal stricture obstruction and anastomotic stenosis caused by invasion, compression of advanced abdominal malignant tumors or other malignant lesions, et cetera, but its effect is single and narrow. At present, for the operation of the pharynx and larynx, a supporting laryngoscope is commonly used in clinic to examine the abnormality of the laryngeal structure in detail, to determine the location and range of the lesion, and to perform biopsy on the lesion tissue when necessary, but the functional indexes of the larynx cannot be obtained through examination, and the supporting laryngoscope is usually a rigid structure and thus must be used under the condition of general anesthesia of a patient. As a result, the application of the supporting laryngoscope is limited, and the supporting laryngoscope has a single and limited effect by only providing a passage for the operation.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, the disclosure provides a hollow vector support multifunctional protection device including a protective head, a pitching mechanism for the protective head, an inner cylinder, an axial movement mechanism for the inner cylinder, and a shell. The protective head includes a flap ring, a plurality of first rotating shafts, a plurality of flaps uniformly arranged on the flap ring through the first rotating shafts, and a torsion spring arranged on the first rotating shafts. The torsion spring is configured to provide a force for opening the plurality of flaps along the first rotating shafts, and the first rotating shafts are provided with limiting structures configured to limit a maximum opening degree of the flaps. One end of the flap ring is connected with a head end of the inner cylinder through a second rotating shaft. Another end of the flap ring is connected with the pitching mechanism through a third rotating shaft. The inner cylinder is arranged in the shell. The protective head extends out of a head end of the shell. A tail end of the inner cylinder is connected with a tail end of the shell through the axial movement mechanism.

Optionally, a flap includes a hollow layer, an interface, and a hole. The interface is arranged at a bottom end of the flap. The hole is arranged at a top end of the flap. The interface is connected with the hole through the hollow layer. The interface is connected with at least one item selected from the group consisting of a gas/liquid transmission and exhaust pipeline and an illumination device.

Optionally, at least one item selected from the group consisting of an inner surface of a flap and an outer surface of the flap is provided with fixing structures by which the flap is configured to fix at least one item selected from the group consisting of a gas/liquid transmission and exhaust pipeline and an illumination device to the flap.

Optionally, a transmission mechanism of the pitching mechanism is selected from the group consisting of a connecting rod transmission mechanism, a steel wire rope transmission mechanism, a belt transmission mechanism, a gear transmission mechanism, a chain transmission mechanism, and a key transmission mechanism.

Optionally, the pitching mechanism is driven by a drive selected from the group consisting of a manual drive, a motor drive, a hydraulic press drive, and a pneumatic press drive.

Optionally, a transmission mechanism of the axial movement mechanism is selected from the group consisting of a screw transmission mechanism, a rack and pinion transmission mechanism, a belt transmission mechanism, a rope transmission mechanism, and a rod transmission mechanism.

Optionally, an outer surface of the flap is curved, and the outer surface of the flap is in contact with a head end of the shell so as to limit an opening degree of the flap when the axial movement mechanism drives the protective head to ascend and to descend.

Optionally, an elastic membrane covers at least one item selected from the group consisting of (1) a gap between the protective head and the shell and (2) gaps among the plurality of flaps.

Optionally, a thin steel wire spiral coil is provided between the protective head and the shell, and the elastic membrane covers an outer surface of the thin steel wire spiral coil.

BRIEF DESCRIPTION OF THE DRAWINGS

Illustrative embodiments of the present disclosure are described in detail below with reference to the figures.

DETAILED DESCRIPTION

The following describes some non-limiting embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

Figure 1:
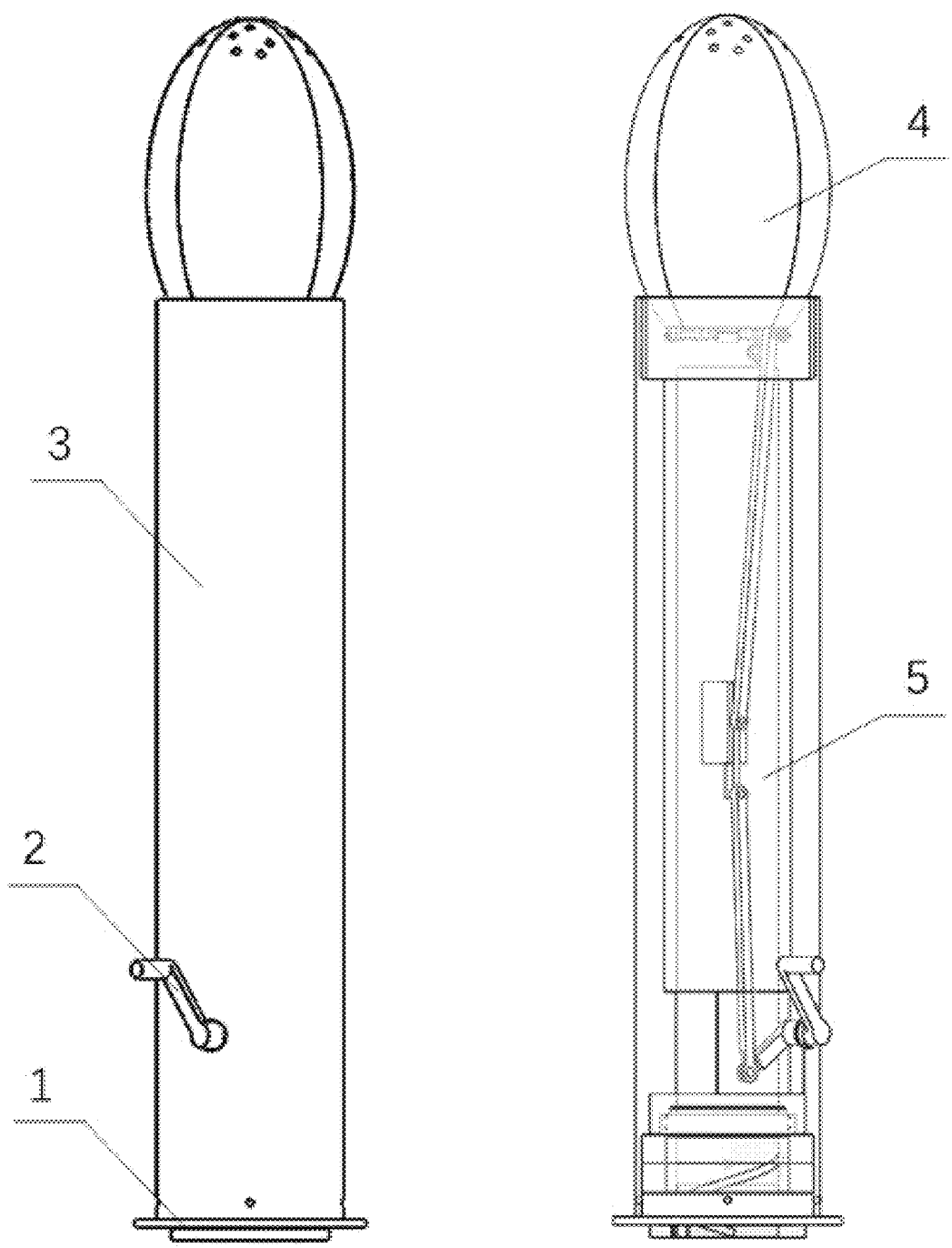
FIG. 1 is an overall structural schematic view of a hollow vector support multifunctional protective device according to an embodiment of the disclosure.

FIG. 1 is an overall structural schematic view of a hollow vector support multifunctional protection device for minimally invasive surgery according to an embodiment of the disclosure. As shown in FIG. 1, the protection device may penetrate into a narrow cavity channel, and a vector support sleeve protective head (hereinafter as "protective head") 4 and an inner cylinder 5 may be configured to move along the axial direction of a shell 3 through an axial movement mechanism for inner cylinder 1. The protective head may be rotated around an axis α through an axial movement mechanism 2, meanwhile, a plurality of flaps of the protective head may be automatically opened, tissue around the cavity channel may be expanded, and an operation space may be supported for a surgical operation. The hollow vector support multifunctional protection device may include a hollow inner cylinder and a protective head. The hollow inner cylinder and the protective head may guide a surgical tool to reach focus tissues, and a flap of the protective head may be provided with gas/liquid transmission and exhaust pipelines which may be used for providing negative pressure and forming a drug transmission channel to assist a surgical operation so that the cavity operation may become more convenient.

The hollow inner cylinder 5 may allow fibers of optical fiber surgical, medical surgical instruments (e.g., forceps, manipulator arms, scalpels, etc.), and sensors (e.g., imaging probes) to pass through itself to a surgical area without damaging surrounding tissue, which may help to improve surgical flexibility, safety, and convenience.

Figure 2A:
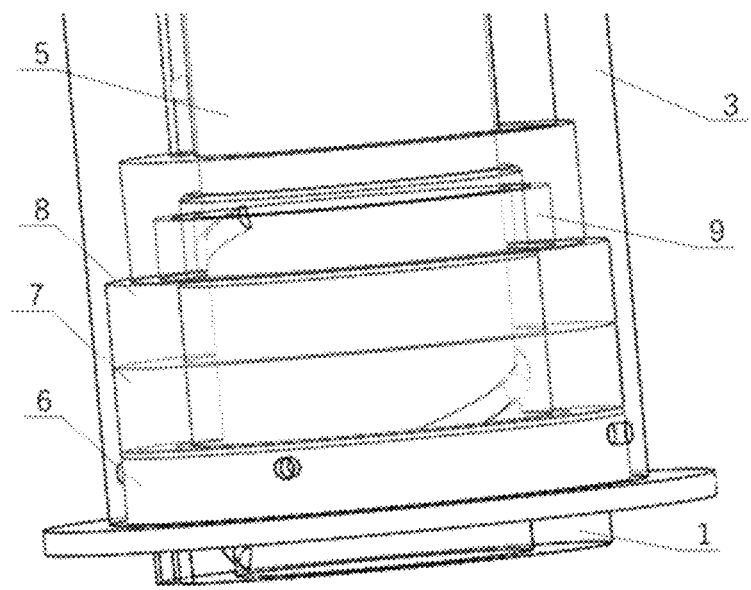
FIG. 2a is a structural view of an axial movement mechanism according to an embodiment of the disclosure.
Figure 2B:
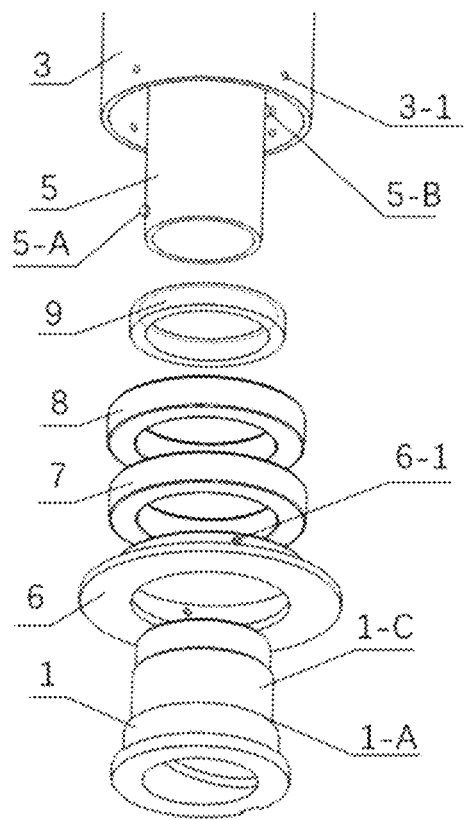
FIG. 2b is an exploded view of an axial movement mechanism according to an embodiment of the disclosure.
Figure 2C:
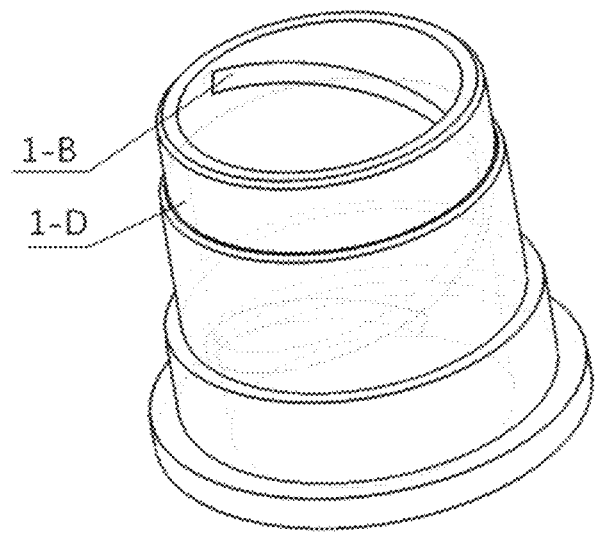
FIG. 2c is a schematic view of a knob according to an embodiment of the disclosure.
Figure 2D:
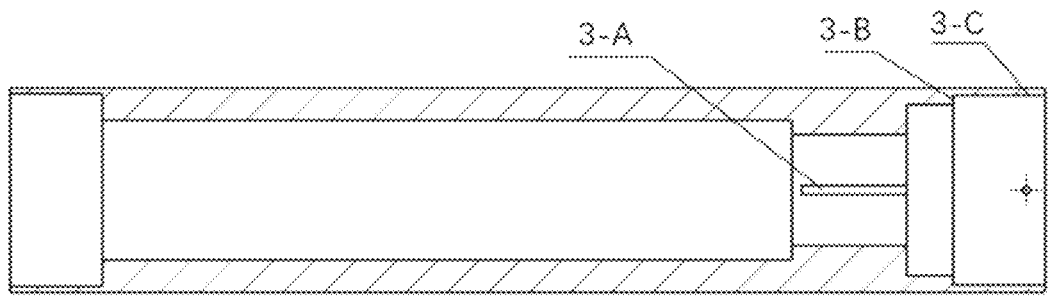
FIG. 2d is a cross-sectional view of a shell according to an embodiment of the disclosure.

Next, FIG. 2a shows an axial movement mechanism of the protective head of the cavity tract surgical protection device along the shell, FIG. 2b shows an exploded view of FIG. 2a, FIG. 2c shows a schematic view of the knob, and FIG. 2d shows a sectional view of the shell. The inner rings of the first bearing 7 and the second bearing 8 of the axial movement mechanism for inner cylinder may be engaged with a face of the knob 1-C, the outer ring may be engaged with a face of the shell 3-C, and the threaded retainer ring 9 may be engaged with a face of the knob 1-D. The bearing retainer ring 6 may be fixedly connected with the shell through a screw 6-1 (or 3-1), and then by combining rotating shaft shoulder 1-A and shell shoulder 3-B relative axial positions of the first bearing and the second bearing with respect to the knob and the shell may be fixed; and the knob may rotate relative to the shell. First salient point 5-A of the inner cylinder may be engaged with knob spiral sliding groove 1-B, and second salient point 5-B of the inner cylinder may be engaged with shell straight sliding groove 3-A.

As a result of such design, when the knob rotates relative to the shell, the inner cylinder may move axially along the linear sliding groove 3-A, namely along the shell, and meanwhile, the protective head may be driven to axially move along the shell. In the present example, the screw pair may have a self-locking function, that is, the screw pair implements self-locking after a lead angle is less than or equal to a friction angle or an equivalent friction angle of the screw pair. After the screw pair is self-locked, the inner cylinder may only be driven to move linearly through the knob, and the inner cylinder cannot drive the knob to rotate. In a practical application, a gear-rack transmission, a belt transmission, a rope transmission, and/or a rod transmission may also implement the above movement other than a spiral transmission as disclosed herein. In terms of power selection, in addition to manual operation disclosed herein, automation may alternately be implemented by a motor drive, a hydraulic drive, a pneumatic drive, and/or a magnetic drive.

In addition, the inner cylinder and the shell in the embodiment may be discrete components. They may be detached and/or assembled conveniently, which may help to enable a simple preoperative disinfection and a simple postoperative cleaning. Optionally, they may be made as a disposable product to avoid cross infection.

Figure 3A:
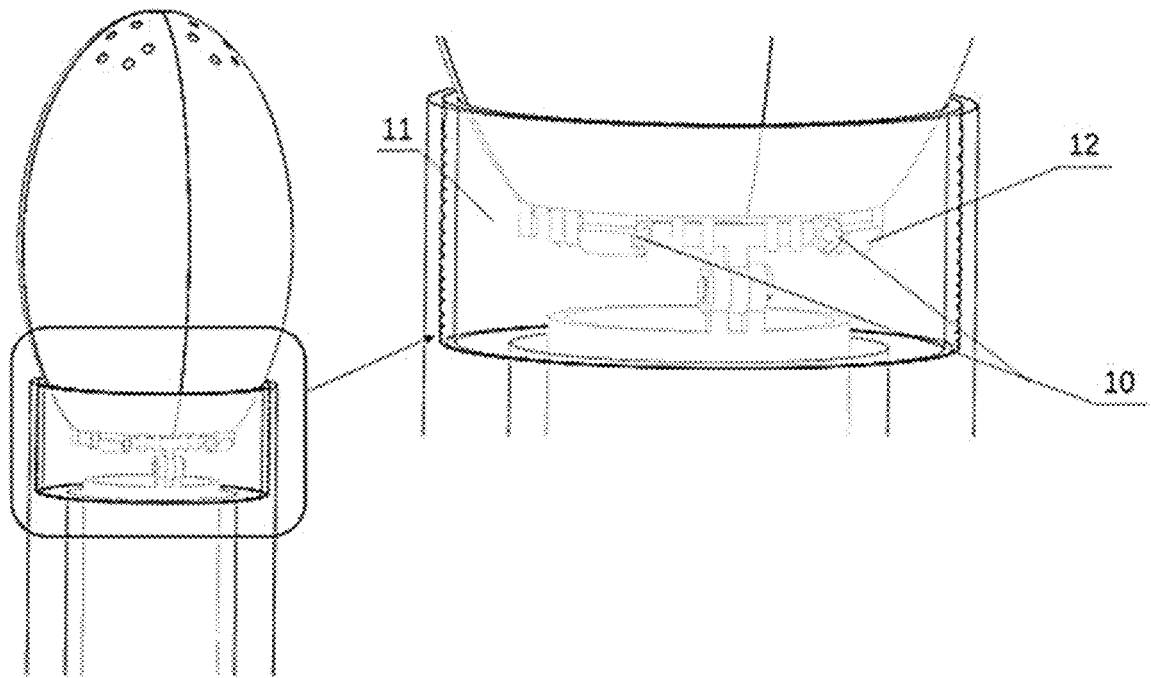
FIG. 3a is an initial state diagram of a protective head according to an embodiment of the disclosure.
Figure 3B:
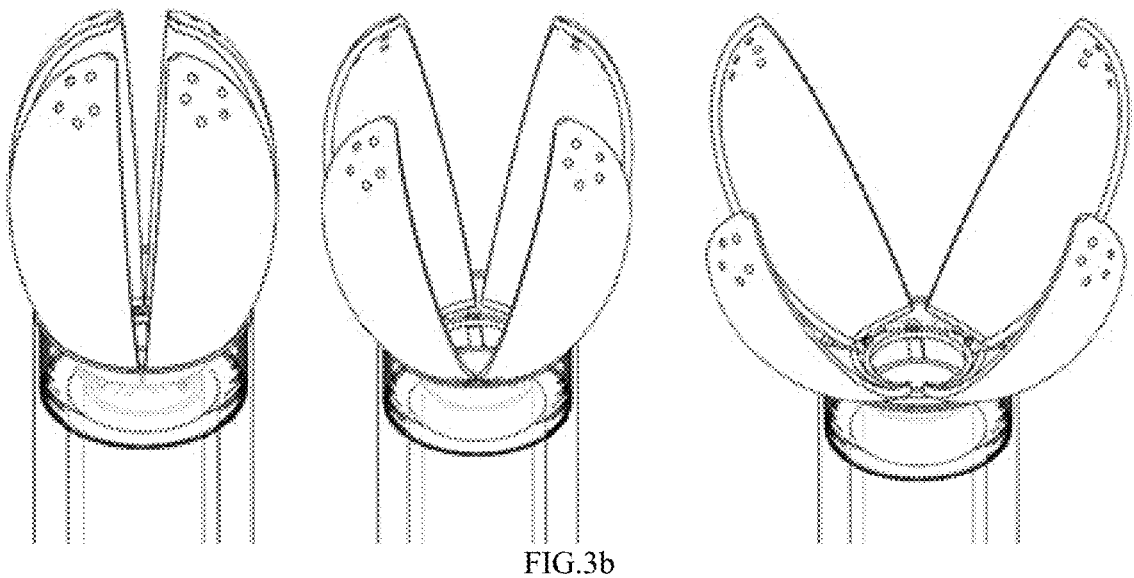
FIG. 3b is a schematic view of a deployment process of flaps of the protective head according to an embodiment of the disclosure.
Figure 3C:
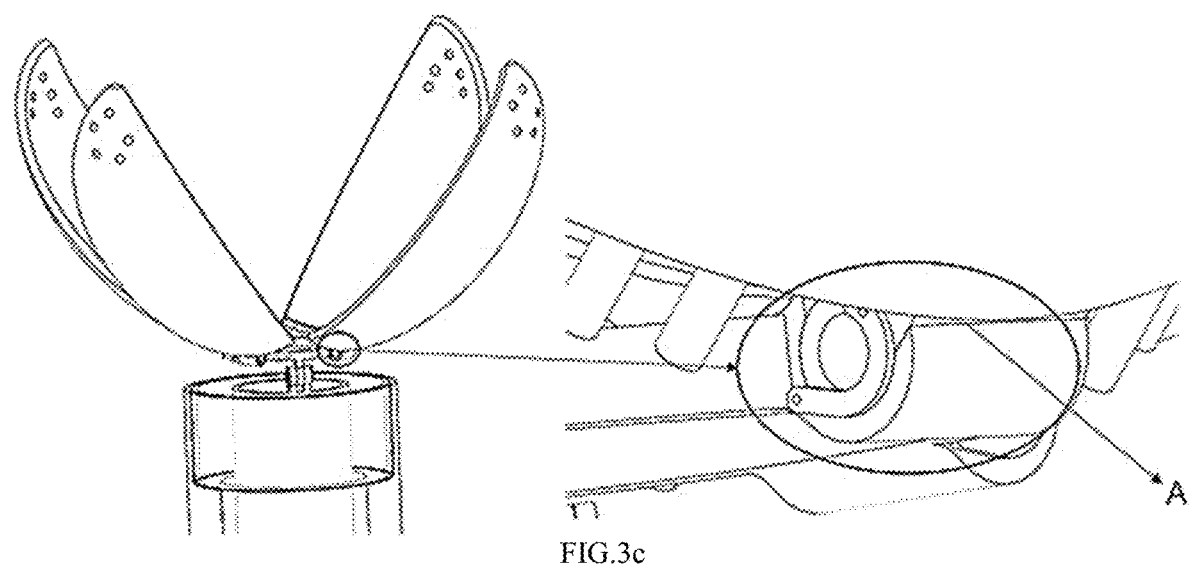
FIG. 3c is a schematic view illustrating a state of the flaps of the protective head opening to a maximum opening degree according to an embodiment of the disclosure.

FIG. 3a shows a view of the initial state of the flaps of the protective head when the flaps of the protective head are closed according to an embodiment of the disclosure. The torsion spring 10 (optionally a leaf spring) connecting the flaps and a flap ring 12 may be in an energy storage state. When the inner cylinder and the protective head move axially along the shell, the leaf spring 10 may drive the flaps to be opened and tangent to the edge of the shell, and the opening degree of the flap of the protective head may increase along with the upward movement of the inner cylinder, as shown in FIG. 3b. When each flap reaches a defined position, as shown in FIG. 3c, the opening degree of the flaps of the protective head may be at the greatest, at this moment, the leaf spring 10 may still have some stored energy to overcome the tension or pressure of the tissue surrounding the lumen. When the flaps need to be closed, the knob may be rotated in the reverse direction to drive the inner cylinder to move downwards, the flaps may be passively closed, and the leaf spring 10 may now store energy. Alternately, in a practical application, the unfolding of the flap of the protective head may be implemented by means of torsion springs, a rope transmission, a gear transmission, a cam transmission, et cetera.

In some embodiments, the closing of the flaps the protective head may be passively implemented through the restriction of the energy storage leaf spring 10 and the shell. In other embodiments, the flaps may also be designed in an actively controllable closed configuration, i.e. the closing of each flap may be controlled. Compared with active closing, the passive closing shown by the embodiment may be simpler in structure and more convenient to assemble and/or disassemble.

Figure 4A:
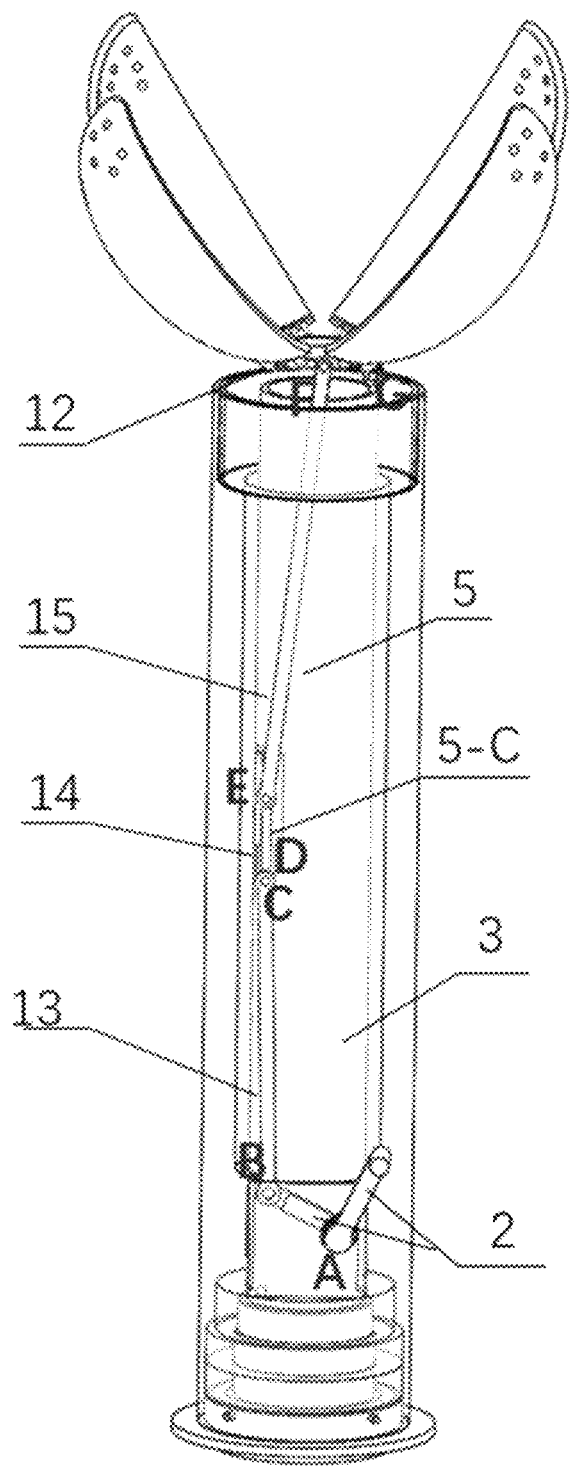
FIG. 4a is a schematic view illustrating a state in which the protective head is raised to the highest position according to an embodiment of the disclosure.
Figure 4B:
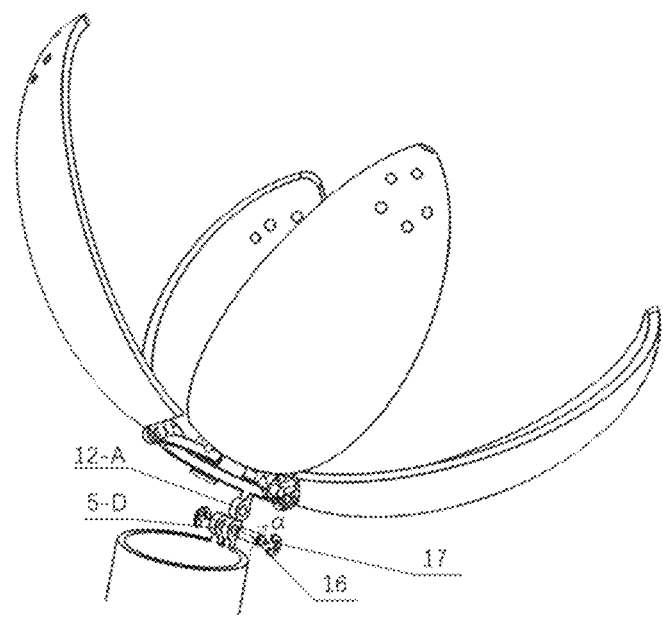
FIG. 4b is a schematic view of an axis α according to an embodiment of the disclosure.
Figure 4C:
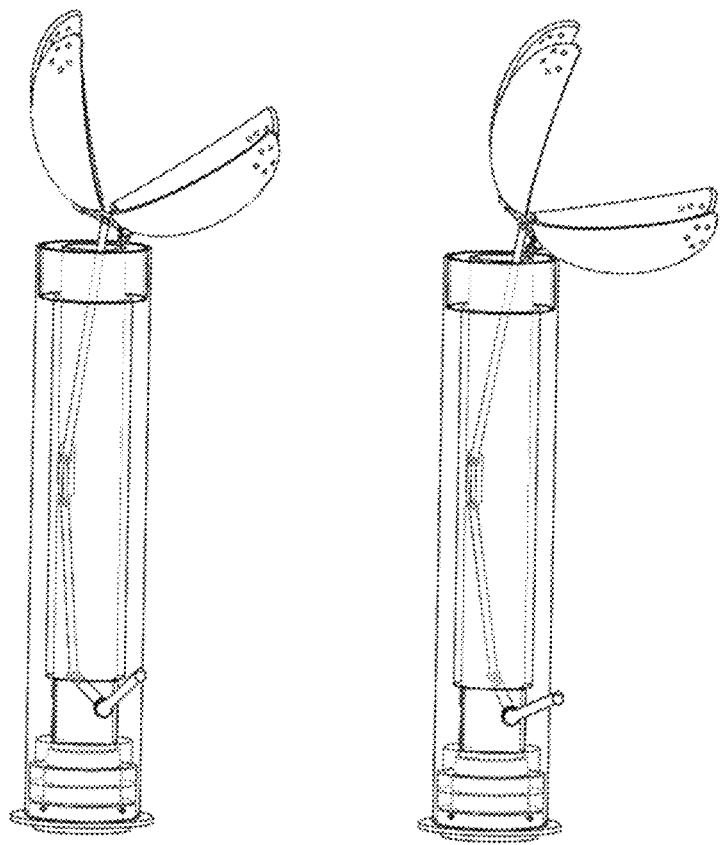
FIG. 4c is a schematic view of the protective head rotating about the axis α according to an embodiment of the disclosure.

FIG. 4a shows a schematic view illustrating a state in which the protective head of the cavity surgical protection device is raised to the highest position and the opening degree is maximum according to an embodiment of the disclosure. The axial movement mechanism for inner cylinder employed in this embodiment may be a double four-bar mechanism. The flap ring 12 may be rotated about an axis α (shown in FIG. 4b) via a double four-bar mechanism by rocking a rocker. The double four-bar mechanism may include a rocker-slider mechanism composed of a shell, a rocker 2, a first connecting rod 13, and a sliding block 14, and a slider-rocker mechanism composed of the sliding block 14, a second connecting rod 15, a rocker 12, and an inner cylinder. The shell and the rocker may form a first hinge pair A, the rocker and the first connecting rod may form a second hinge pair B, the first connecting rod and the sliding block may form a third hinge pair C, the sliding block and the inner cylinder may form a sliding pair D, the slider and the second connecting rod may form a fourth hinge pair E, the second connecting rod and the flap ring may form a fifth hinge pair F, and the flap ring and the inner cylinder may form a sixth hinge pair G. When the knob pushes the inner cylinder and the protective head to the highest position, the rocker may be rotated to drive the flaps of the protective head to rotate around the axis α through transmission of the double four-bar mechanism, and the schematic view of the middle process and the maximum rotation angle status are shown in FIG. 4c. In a practical application, besides rotating the rocker manually, the rocker may also be driven to rotate by means of automatic technology, such as a motor drive, a hydraulic drive, a pneumatic drive, et cetera. Besides rotating the protective head around the axis α through a double four-bar mechanism, the rotation may also be implemented through a wire rope transmission, a belt transmission, a gear transmission, a chain transmission, a key transmission, et cetera.

Figure 5A:
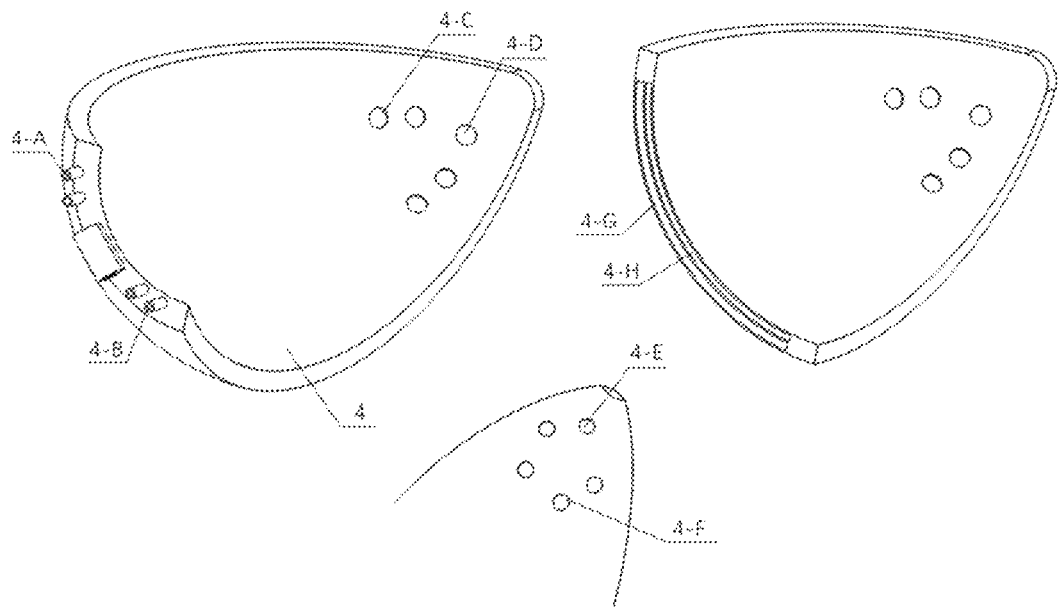
FIG. 5a is a schematic view of a hollow flap according to an embodiment of the disclosure.

FIG. 5a is a schematic view of the flaps of protecting a head. In such example, each flap may be of a double-layered hollow structure, respectively an outer hollow layer 4-G and an inner hollow layer 4-H. The two hollow layers are respectively communicated with an outer pipe interface 4-A and an inner interface 4-B, and the outer interface and the inner interface are connected with gas/liquid transmission and exhaust pipelines, so that the flaps have the effect of expanding surrounding tissues, and further being able to inhale and blow air (through holes shown in FIGS. 4-D and 4-E) or deliver medicines for the operation. The outer interface and the inner interface may also be connected with an illumination circuit to provide illumination for the cavity operation space (shown in FIGS. 4-C and 4-F), so that the operation is convenient. A certain gap is formed between the inner cylinder and the shell, and the gas/liquid transmission and exhaust pipelines and the illumination circuit are connected to the outside through the gap between the inner cylinder and the shell, so that the influence of the pipeline and the circuit on human tissues is avoided, particularly the surrounding human tissues are prevented from scratch and damage which may cause secondary injury.

Figure 5B:
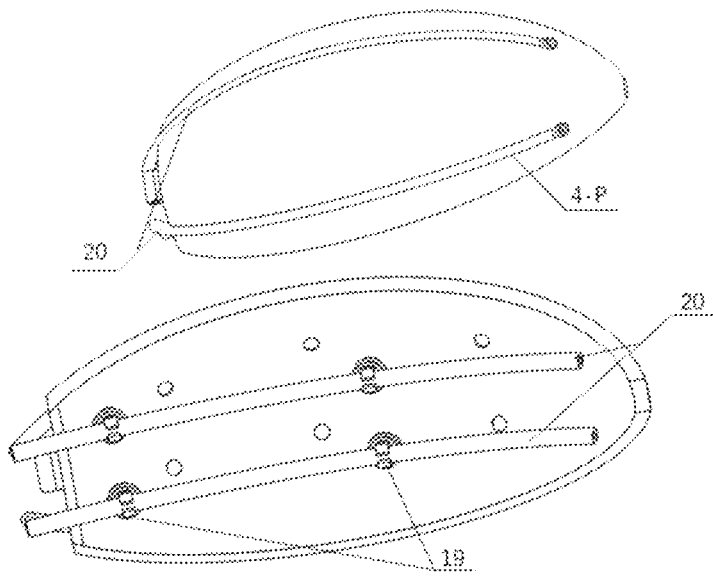
FIG. 5b is a schematic view of a non-hollow flap according to an embodiment of the disclosure.

In practice, besides this example of the flaps being of a double-layered hollow structure, in another example the flaps may be of a non-hollow structure, in which the lines of the gas/liquid transmission and exhaust pipelines 20 and the illumination device are instead clamped to inner and outer surfaces of the flaps by means of a fixing structure 19 (e.g. a clip); or pipeline and line grooves 4-P are formed on the inner and outer surfaces, gas delivery pipelines, drug delivery pipelines and lines are pressed into the grooves, as shown in FIG. 5b. The protective head is of a multi-flap structure, and the number, the shape, the length and the diameter of the protective head may be individually designed according to requirements of different operation positions and the protective head may be divided into different models.

In structure of the protective head, the gas/liquid transmission and exhaust pipelines are detachably connected with the protective head through the interface, so the gas/liquid transmission and exhaust pipelines are convenient to mount and dismount, simplifying the disinfection and cleaning process, and the gas/liquid transmission and exhaust pipelines are disposable, so as to be able to avoid cross infection.

Figure 6:
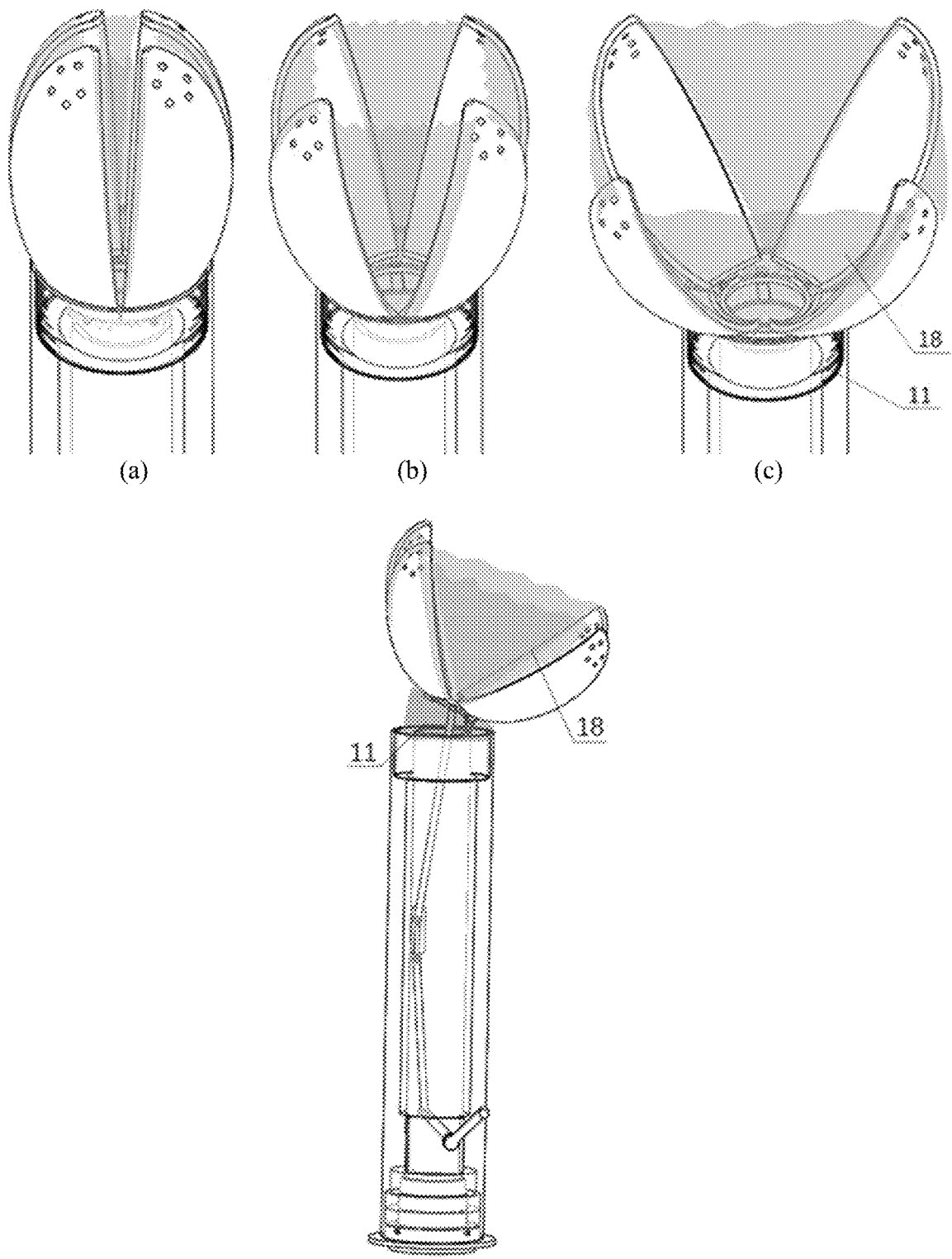
FIG. 6 is a schematic view of a collapsible elastic membrane according to an embodiment of the disclosure.

Portions between the protective head and the shell of the protection device and between the flaps of the protective head are covered with a collapsible and inward-retracted elastic membrane, as shown as 11 and 18 in FIG. 6, the elastic membrane 11 is unfolded or folded along with the rising/falling of the inner cylinder and the rotation of the flap ring, and the elastic membrane 11 is unfolded or folded along with the unfolding/closing of the flaps of the protective head of the cavity surgery protection device, so that the effect of isolating the cavity surgery protection device from surrounding tissues is achieved. In practice, the material of the elastic membrane may be a high molecular or biological material such as rubber, plastic, or the like. A thin steel wire spiral ring is arranged inside the elastic membrane 11 to prevent the elastic membrane 11 from collapsing; the elastic membrane is optionally a transparent elastic membrane, so that the operation condition of the surgical area may be observed, facilitating the control on operation safety.

The hollow vector support multifunctional protection device for minimally invasive surgery provided in the embodiment of the invention may have at least three active degrees of freedom and one passive degree of freedom. The three active degrees of freedom include: the protection device rolling, namely the protection device integrally rotating around the axial direction of the inner cylinder; the inner cylinder rising and falling along the axial direction; the head end of the protection device pitching. One passive degree of freedom includes: the flaps of the protective head being opened and closed by axial lifting or lowering of the inner cylinder and the torsion spring.

It should be noted that the protective head, the pitching mechanism for protective head and the axial movement mechanism for inner cylinder provided in this embodiment are all optional structures; these structures may be substituted for other structures that perform the same function in this or related fields to achieve the objects of the disclosure, and such other structures are not exemplified in this embodiment.

Various embodiments of the disclosure may have one or more of the following effects.

The protection device disclosed by the embodiment greatly increases the safety and convenience of the cavity surgery operation. Although the relevant operations illustrated in this embodiment are manual (i.e., operated by the operator), in practice, automatically controllable operations may also be implemented in conjunction with automated techniques.

In some embodiments, the disclosure may provide a hollow vector support multifunctional protection device for minimally invasive surgery, which may be applied to cavity and intestinal tract surgery in various medical fields, including operation on an oral cavity, a nasal cavity, a thoracic cavity and an abdominal cavity; and operation on large intestine, small intestine, duodenum, rectum, airway and ear canal, et cetera.

In other embodiments, the disclosure may provide a hollow vector support multifunctional protection device, which may be applied to minimally invasive surgery of cavities such as oral cavities, throat parts, digestive tracts, respiratory tracts, thoracic cavities, abdominal cavities, et cetera. As to the flaps of the protective head of the protection device, their opening degree may be adjusted through an axial movement mechanism for inner cylinder to protect a surgical area, and the size of the surgical area may be freely adjusted. The protective head may also rotate outwards through a pitching mechanism for protective head, which may help to increase a surgical visual field so that vector adjustment of the protective head and the flap may be implemented. The protective head and the flap may be adjusted in direction, force, and/or size as required.

In further embodiments, disclosure may provide a hollow vector support multifunctional protection device, in which the flaps on the protective head may be configured to protect the surgical area by adjusting the opening degree through the axial movement mechanism for the inner cylinder, the size of the surgical area may be freely adjusted, and the protective head may rotate outwards through the pitching mechanism for the protective head to increase surgical visual field.

Optionally, each flap may be provided with a gas/liquid transmission and exhaust passage and/or a illumination device so that multiple functions of lighting, flushing, administration, cleaning, disinfecting, hemostasis, and providing a supporting passage for surgical tools such as laser scalpels may be integrated. Wounds in the surgical area may be reduced by covering with an elastic membrane between the protective head and the shell and/or between the flaps, or the like.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

What is claimed is:

1. A hollow vector support multifunctional protection device, comprising: a protective head, a pitching mechanism for the protective head, an inner cylinder, an axial movement mechanism for the inner cylinder, and a shell, wherein:
   the protective head comprises a flap ring, a plurality of first rotating shafts, a plurality of flaps uniformly arranged on the flap ring through the plurality of first rotating shafts, and a torsion spring arranged on the plurality of first rotating shafts, wherein:
      the torsion spring is configured to provide a force for opening the plurality of flaps along the plurality of first rotating shafts, and
      the plurality of first rotating shafts are provided with limiting structures configured to limit a maximum opening degree of the flaps;
   one end of the flap ring is connected with a head end of the inner cylinder through a second rotating shaft;
   another end of the flap ring is connected with the pitching mechanism through a third rotating shaft;
   the inner cylinder is arranged in the shell;
   the protective head extends out of a head end of the shell; and
   a tail end of the inner cylinder is connected with a tail end of the shell through the axial movement mechanism.

2. The device according to claim 1, wherein:
   each flap comprises a hollow layer, an interface, and a hole;
   the interface is arranged at a bottom end of the flap;
   the hole is arranged at a top end of the flap;
   the interface is connected with the hole through the hollow layer; and
   the interface is connected with at least one item selected from the group consisting of a gas and/or liquid transmission and exhaust pipeline and an illumination device.

3. The device according to claim 1, wherein at least one item selected from the group consisting of an inner surface of a flap and an outer surface of the flap is provided with fixing structures by which the flap is configured to fix at least one item selected from the group consisting of a gas and/or liquid transmission and exhaust pipeline and an illumination device to the flap.

4. The device according to claim 1, wherein a transmission mechanism of the pitching mechanism is selected from the group consisting of a connecting rod transmission mechanism, a steel wire rope transmission mechanism, a belt transmission mechanism, a gear transmission mechanism, a chain transmission mechanism, and a key transmission mechanism.

5. The device according to claim 1, wherein the pitching mechanism is driven by a drive selected from the group consisting of a manual drive, a motor drive, a hydraulic press drive, and a pneumatic press drive.

6. The device according to claim 1, wherein a transmission mechanism of the axial movement mechanism is selected from the group consisting of a screw transmission mechanism, a rack and pinion transmission mechanism, a belt transmission mechanism, a rope transmission mechanism, and a rod transmission mechanism.

7. The device according to claim 1, wherein:
an outer surface of a flap is curved; and
the outer surface of the flap is in contact with a head end of the shell so as to limit an opening degree of the flap when the axial movement mechanism drives the protective head to ascend and to descend.

8. The device according to claim 1, wherein an elastic membrane covers at least one item selected from the group consisting of (1) a gap between the protective head and the shell and (2) gaps among the plurality of flaps.

9. The device according to claim 8, wherein:
a thin steel wire spiral coil is provided between the protective head and the shell; and
the elastic membrane covers an outer surface of the thin steel wire spiral coil.

* * * * *